United States Patent [19]

Hepburn et al.

[11] Patent Number: 4,947,835
[45] Date of Patent: Aug. 14, 1990

[54] ADJUSTABLE SPLINT ASSEMBLY

[75] Inventors: George R. Hepburn, Severna Park; Dror Paley, Baltimore, both of Md.

[73] Assignee: Dynasplint Systems, Inc., Baltimore, Md.

[21] Appl. No.: 333,395

[22] Filed: Apr. 5, 1989

[51] Int. Cl.$^5$ ............................................... A61F 5/04
[52] U.S. Cl. ................................. 128/84 R; 128/80 F; 128/84 B; 128/85; 606/56
[58] Field of Search ................. 128/80 R, 80 A, 80 B, 128/80 C, 80 F, 80 E, 84 B, 84 R; 606/54, 55, 56, 57, 59, 72, 73, 74, 87, 88

[56] References Cited

U.S. PATENT DOCUMENTS

| | | | |
|---|---|---|---|
| 1,334,596 | 3/1920 | Crouch | 128/85 |
| 2,020,262 | 11/1935 | Longfellow | 128/84 B |
| 2,055,024 | 9/1936 | Bittner, Jr. | 606/56 |
| 4,033,340 | 7/1977 | Kalnberz | 606/56 |
| 4,397,308 | 8/1983 | Hepburn | 128/80 F |

Primary Examiner—Robert A. Hafer
Assistant Examiner—Charles H. Sam
Attorney, Agent, or Firm—Larson and Taylor

[57] ABSTRACT

An adjustable splint assembly comprises of an adjustable splint device and a fixator device, said adjustable splint device comprising a distal strut and a proximal strut pivotably connected to said distal strut, one of said struts having at one end a pivotably mounted head portion defining a cam surface, an adjustable biasing means mounted within the other strut and biased into engagement with said cam surface for applying a quantifiable force tending to align or approximate said distal and proximal struts, said fixator device comprising a right ring and a left ring, two or more surgical wires for implanting through a bone, with said wires connected at each end to the periphery of the right ring and crossing each other substantially near the center axis of said right ring, two or more surgical wires similarly connected to and crossing within the left ring, means for connecting said surgical wires to the right ring and left ring, and upper rod connected at one end to the left ring and at the other end to the right ring, a lower rod connected at one end to the left ring and at the other end to the right ring on the sides of the rings opposite the upper rod, means for connecting said upper rod and lower rod to the right ring and left ring, a clamping assembly slidably mounted on the distal strut of said adjustable splint device, means for securing said clamping assembly to the distal strut, means for connecting said clamping assembly to the right ring of said fixator device, and means for securing said adjustable splint assembly to a limb.

15 Claims, 8 Drawing Sheets

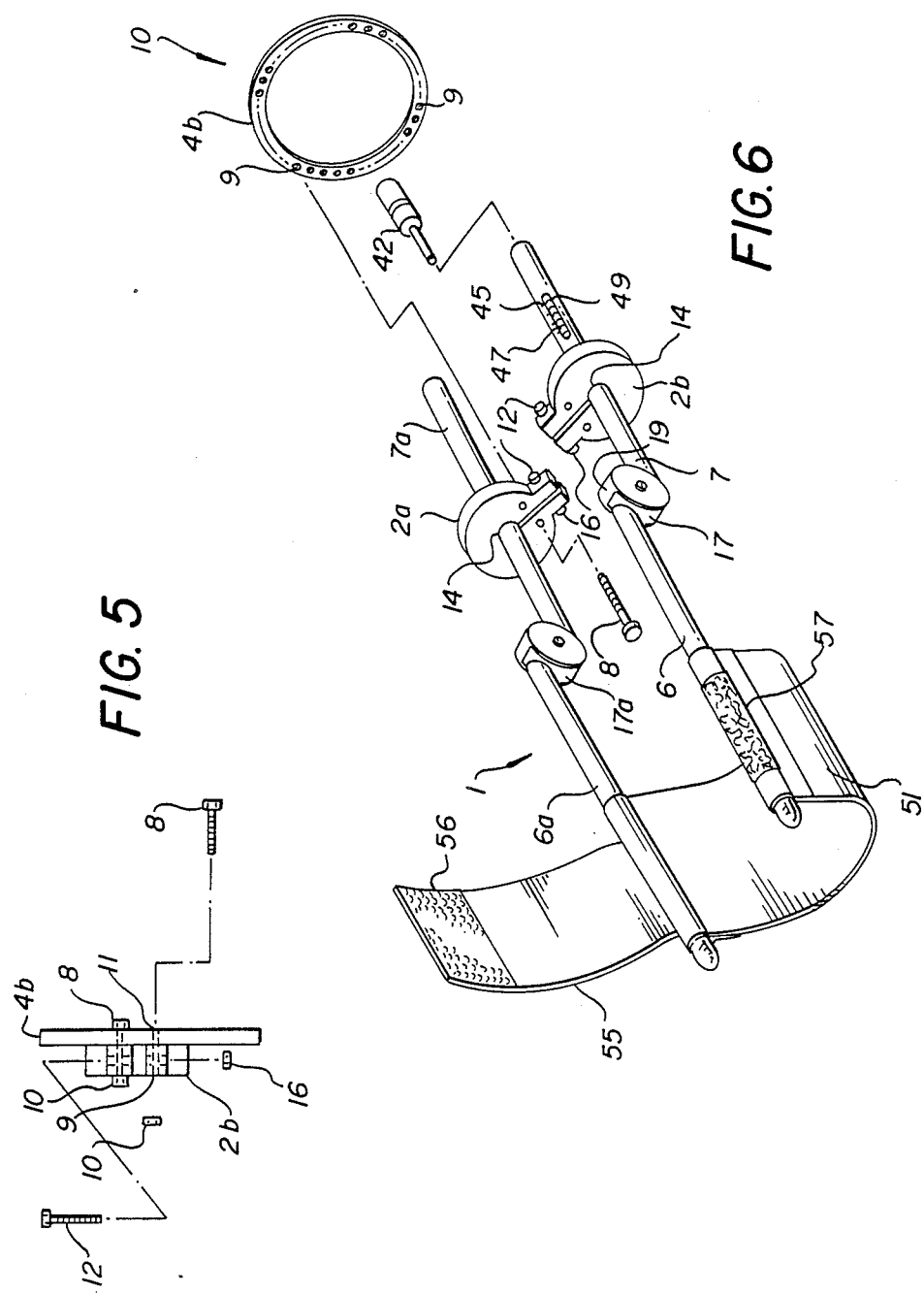

ADJUSTABLE SPLINT ASSEMBLY

BACKGROUND OF THE INVENTION

FIELD OF THE INVENTION

This invention relates to an adjustable splint assembly. More particularly, this invention relates to the combination of an adjustable splint device and an external fixator device, useful for therapeutical treatment of impairments in body joints and the like from flexion and extension contractures, weakness in the supporting musculature, or some other malady inhibiting the integrity of the body joint in accomplishing flexion or extension.

People often develop flexion and extension contractures in body joints such as knee joints or elbow joints from many and various causes. Weakness, disuse, fractures, surgeries, traumatic injuries, illness and other causes have been known to cause loss of ability to extend or flex the knee joint or elbow joint. With respect to surgery in particular, a common, adverse post-operative effect of Ilizarov orthopedic surgery on a leg or an arm, is knee joint or elbow joint contracture or loss of range of motion. In the early 1950's, Prof. Ilizarov of the USSR developed an external fixator device for treating bone injuries using essentially a bloodless surgery technique. The device consists of two or more metal rings surrounding the limb to be treated, with wires surgically implanted through the skeletal part and connected to the metal rings. Tension is maintained between the rings in order to place forces on the bone and facilitate treatment. In the United States, this device has been approved for treatment of the following indications:
1. Fracture fixation.
2. Pseudoarthroses of long bones.
3. Limb lengthening.
4. Correction of bony or soft tissue deformities or defects.

As mentioned above, a common effect of this treatment is joint contracture or loss of range of motion. However, no device presently exists to reduce flexion contractures of knee joints or elbow joints that often result from Ilizarov surgery, by adjustable, quantifiable pressure as does the adjustable splint assembly described herein.

Many splint devices and mechanisms have been designed to be influential at the knee, elbow, etc., either for support or for mobilizing the joints. Illustrations of such devices are those described in U.S. Pat. Nos. 3,055,359; 3,785,372; 3,799,159; 3,928,872; 4,397,308; 4,485,808; 4,508,111; 4,538,600; 4,657,000. However, all of these devices are not designed to reduce knee joint or elbow joint flexion or extension contractures resulting from or related to surgery using an Ilizarov External Fixator, nor can these devices be tolerated by the patient population for a long enough period to effectively reduce a contracture.

OBJECTS OF THE INVENTION

Accordingly, it is an object of the invention to provide an improved splint assembly incorporating a fixator device such as an Ilizarov External Fixator, for reducing flexion and extension contractures about a body joint, particularly a knee joint or an elbow joint.

Yet another object of the invention is to provide such an adjustable splint assembly incorporating an external fixator device, which allows easy gradual adjustment to the quantifiable force desired on an extremity acting across a body joint, particularly a knee joint or an elbow joint.

A further object of the invention is to provide an improved adjustable splint assembly, for providing support to a limb around a body joint, particularly a limb around a knee joint or an elbow joint.

SUMMARY OF THE INVENTION

These and other objects of the invention are obtained by an adjustable splint assembly comprised of an adjustable splint device and a fixator device, said adjustable splint device comprising a distal strut and a proximal strut pivotably connected to said distal strut, one of said struts having at one end a pivotably mounted head portion defining a cam surface, an adjustable biasing means mounted within the other strut and biased into engagement with said cam surface for applying a quantifiable force tending to approximate or align said distal and proximal struts, said fixator device comprising a right ring and a left ring, two or more surgical wires for implanting through a bone, with said wires connected at each end to the periphery of the right ring and crossing each other substantially near the center axis of said right ring, two or more surgical wires similarly connected to and crossing within the left ring, means for connecting said surgical wires to the right ring and left ring, an upper rod connected at one end to the left ring and at the other end to the right ring, a lower rod connected at one end to the left ring and at the other end to the right ring on the sides of the rings opposite the upper rod, means for connecting said upper rod and lower rod to the right ring and left ring, a clamping assembly slidably mounted on the distal strut of said adjustable splint device, means for securing said clamping assembly to the distal strut, means for connecting said clamping assembly to the right ring of said fixator device, and means for securing said adjustable splint assembly to a limb.

In a preferred embodiment, the present invention comprises a pair of distal struts, a pair of proximal struts and an Ilizarov External Fixator ring, each member of the pair of distal struts being pivotably connected to a member of the proximal struts, with said members of the proximal pair being spaced apart a distance to accommodate limb parts proximal to the limb joint and said members of the distal pair being spaced apart a distance to accommodate attachment to opposite sides of the Ilizarov ring, at least one of said struts having at one end a pivotably mounted head portion defining a cam surface, an adjustable biasing means mounted within the strut pivotably connected to said cam surface-containing strut and biased into engagement with said cam surface, for applying a quantifiable force tending to align or approximate the cam surface-containing strut with the adjustable biasing means containing strut, each member of the pair of distal struts being slidably mounted within a clamping assembly, means for tightening said clamping assemblies to grasp securely the distal struts, each of said clamping assemblies connected to the Ilizarov External Fixator ring, means for connecting said clamping assemblies to the Ilizarov External Fixator ring, and means provided at least said pair of proximal struts for securely holding therebetween proximal parts of a limb.

In one aspect of the invention, the adjustable splint is provided with a telescoping wire assembly on the proximal struts whereby the adjustable splint is secured to the limbs. This slidably adjustable wire assembly feature enables the splint device of the invention to accommodate various limb lengths. In addition, novel snap-on comfort pads attachable to the struts of the splint device provide greater patient comfort.

Another aspect of the invention involves a novel cuff for attaching the splint device to a limb which cuff is designed to accommodate limbs of varying circumferences.

BRIEF DESCRIPTION OF THE DRAWINGS

The invention will appear more clearly from the following detailed description when taken in connection with the following drawings which show by way of example a preferred embodiment of the invention:

IN THE DRAWINGS

Figure 1:
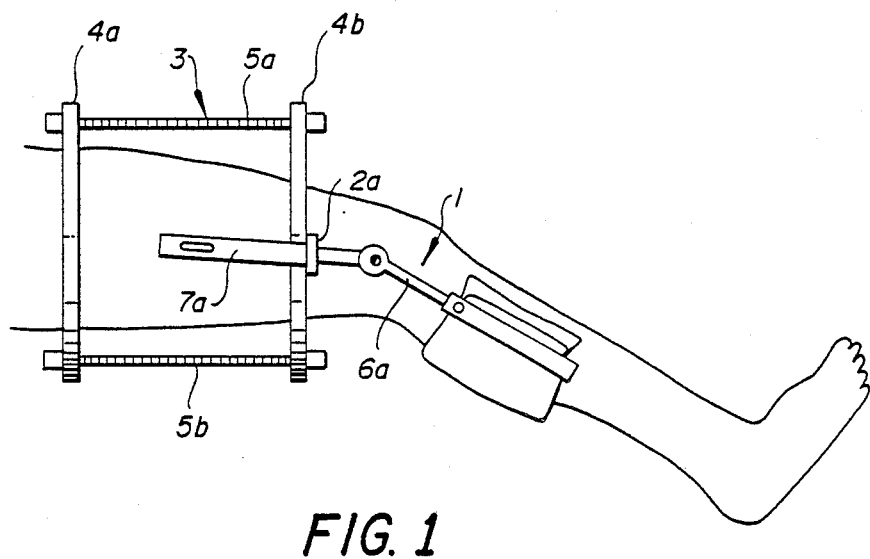
Figure 2:
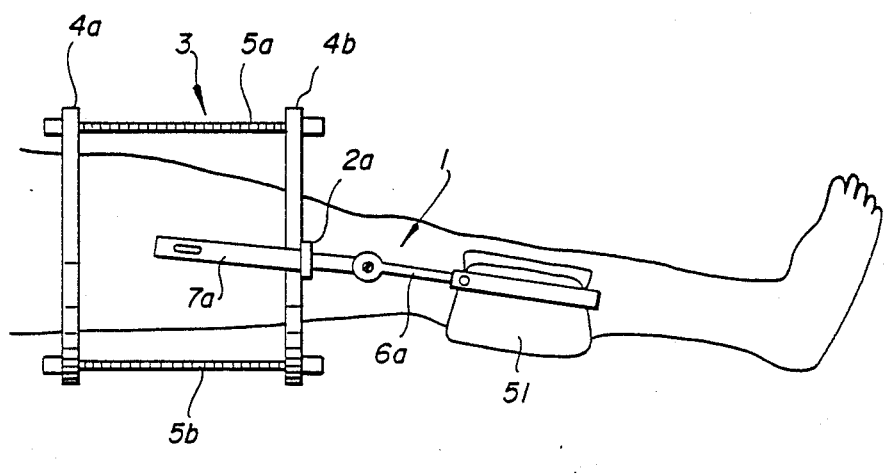
Figure 3:
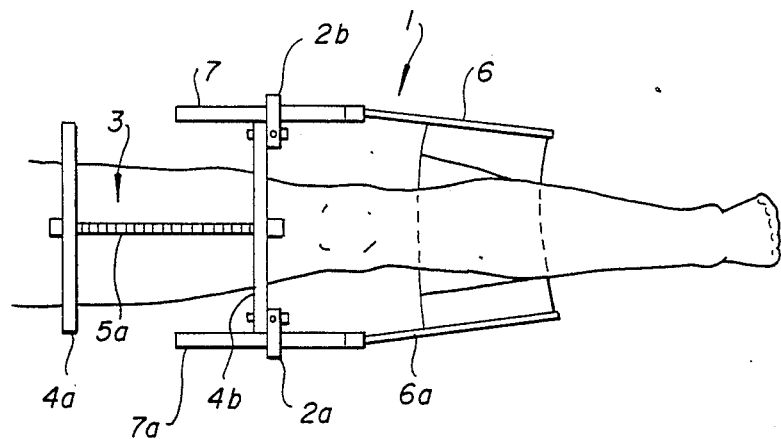
Figure 4:
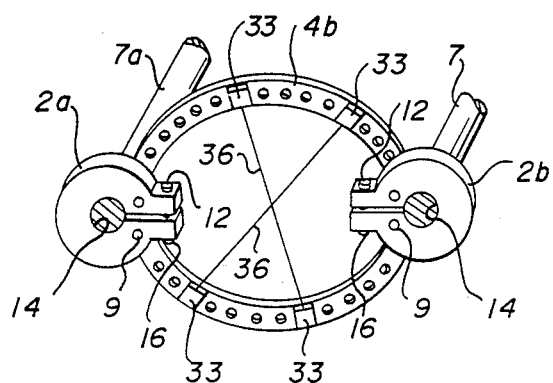
Figure 7:
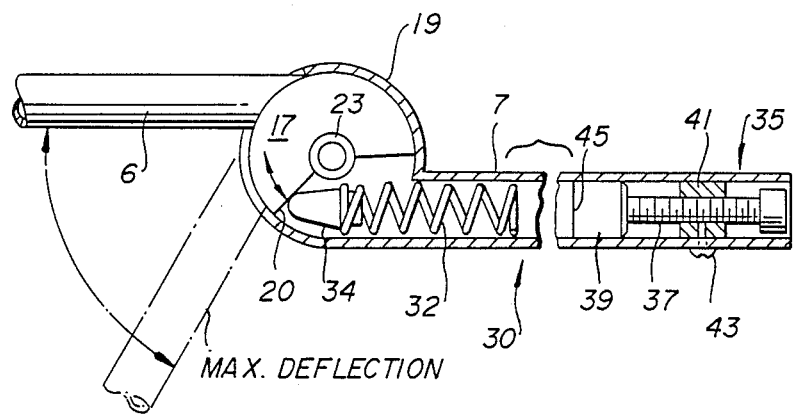
Figure 8:
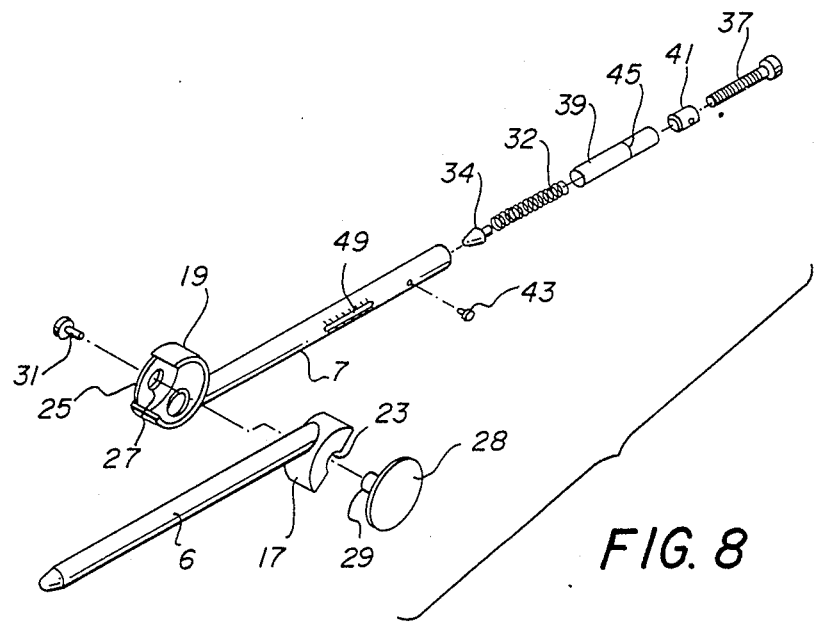
Figure 9:
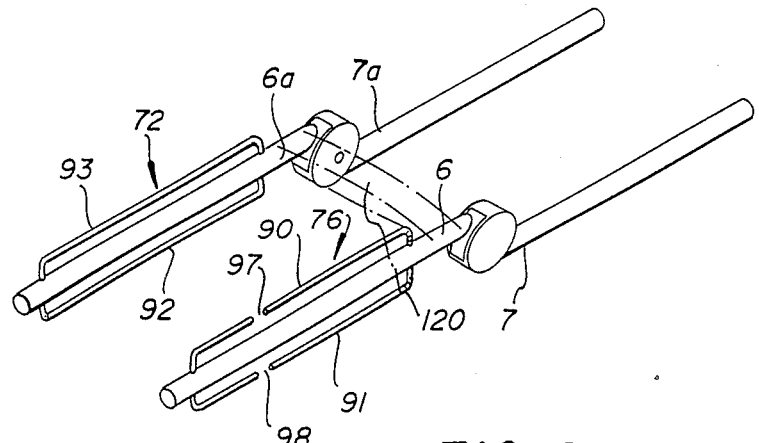
Figure 10:
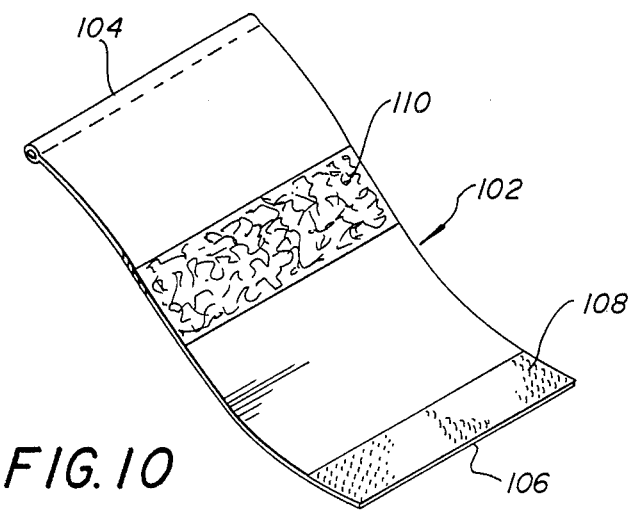
Figure 11:
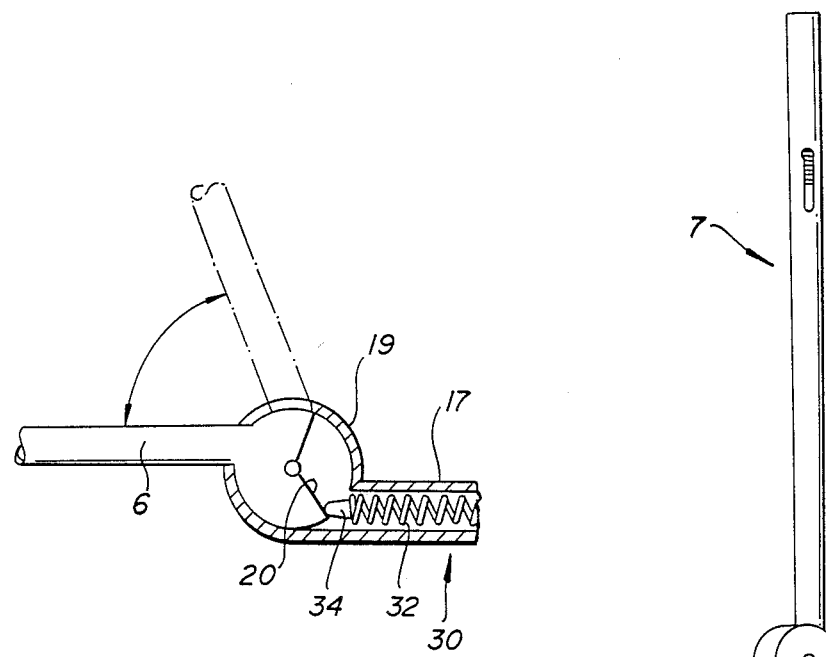
Figure 12:
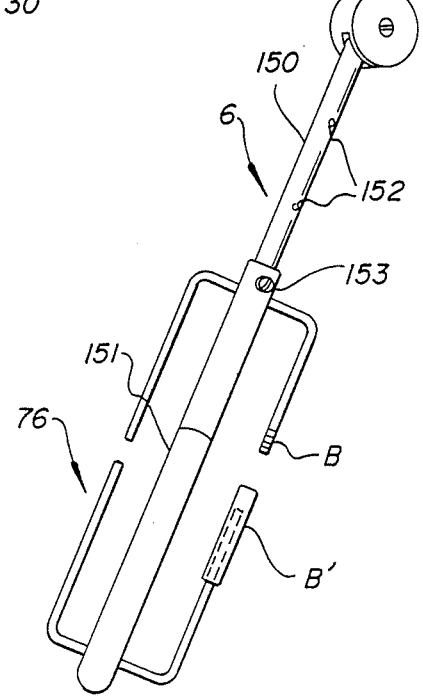
Figure 13:
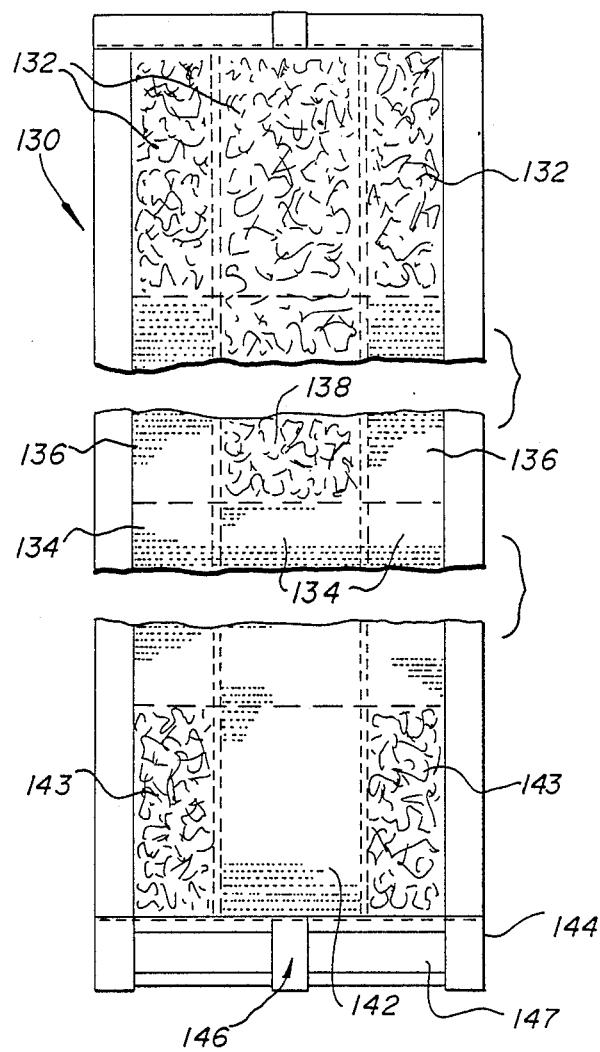
Figure 14:
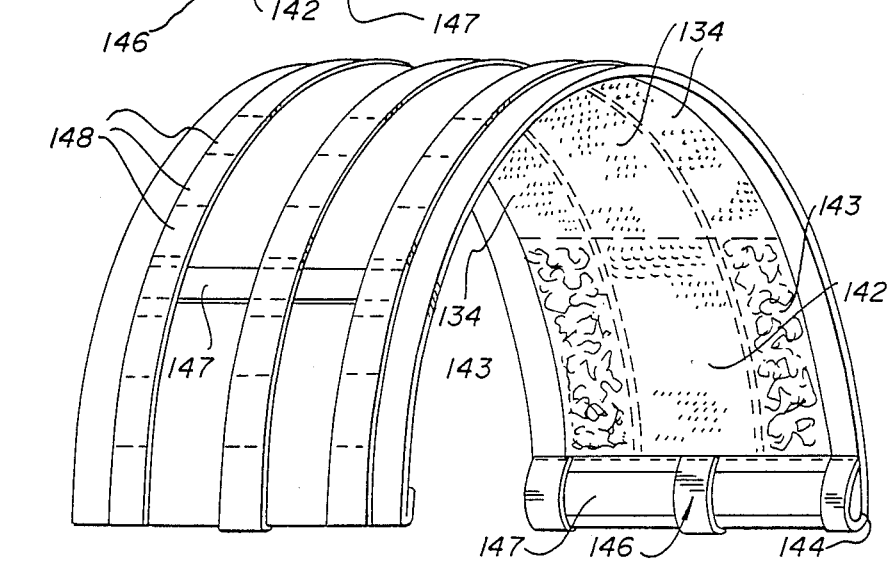
Figure 15:
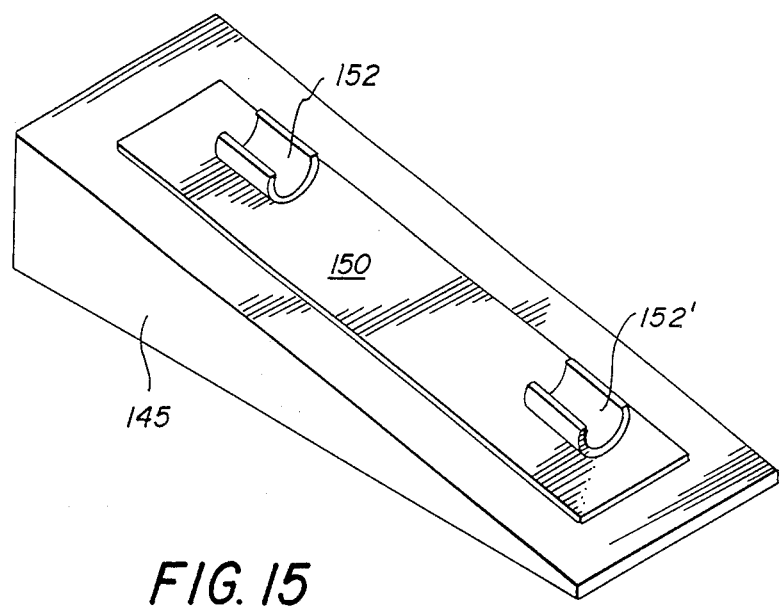
Figure 16:
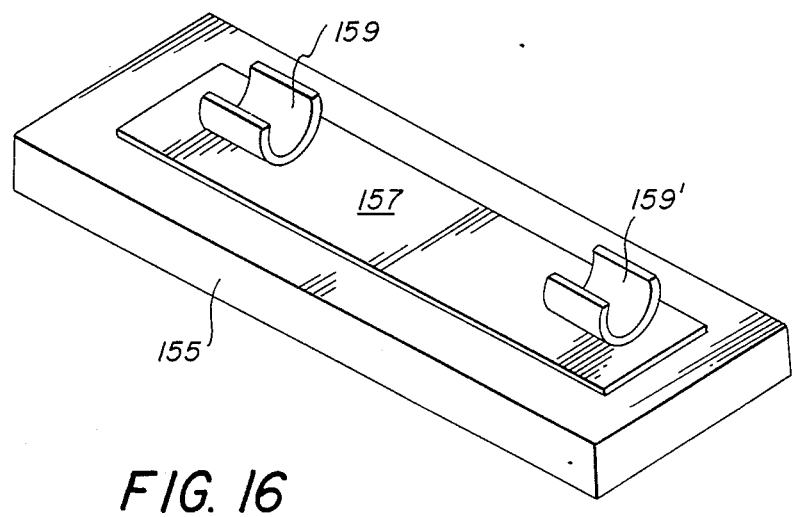

FIG. 1 is a side perspective view of the adjustable splint for reducing flexion contractures incorporating an Ilizarov External Fixator, showing minimum deflection of the proximal strut;

FIG. 2 is a side perspective view of the adjustable splint for reducing flexion contractures incorporating an Ilizarov External Fixator, showing maximum deflection of the proximal strut;

FIG. 3 is a top perspective view of the adjustable splint for reducing flexion contractures incorporating an Ilizarov External Fixator;

FIG. 4 is a front perspective view of an Ilizarov External Fixator ring together with two clamping assemblies for connecting to the distal struts of the adjustable splint;

FIG. 5 is a side perspective view of an Ilizarov External Fixator ring and means connecting same to two clamping assemblies;

FIG. 6 is a perspective, exploded view in part of an Ilizarov External Fixator ring together with the adjustable splint for reducing flexion contractures;

FIG. 7 is a perspective view of one distal and one proximal strut assembly of the adjustable splint of the invention for reducing flexion contractures wherein a strut is broken away to show the adjustable spring-loaded means mounted therein;

FIG. 8 is a perspective, exploded view of the splint device of FIG. 6;

FIG. 9 is a perspective view of the splint device provided with a "break apart" wire assembly for mounting of the means by which the device is secured to the limb;

FIG. 10 is a cuff designed for attachment to the wire assembly shown in FIG. 9;

FIG. 11 is a perspective view of one distal and one proximal strut assembly of the adjustable splint of the invention for reducing extension contractures wherein a strut is broken away to show the adjustable spring-loaded means mounted therein;

FIG. 12 is a perspective view of the splint device provided with a telescoping slidable adjustable wire assembly for mounting of the means by which the device is secured to the limb;

FIG. 13 is a plan view of the outside of another cuff for attachment to the wire assembly designed to accommodate limbs of varying circumferences;

FIG. 14 is a perspective view of the cuff shown in FIG. 13;

FIG. 15 is a perspective view of a wedge-type comfort pad for use in combination with the adjustable splint of the invention; and FIG. 16 is a perspective view of a rectangular-type comfort pad for use in combination with the adjustable splint of the invention.

DESCRIPTION OF THE PREFERRED EMBODIMENTS

Referring to FIGS. 1-3, an adjustable splint device 1 is shown in combination with an Ilizarov External Fixator 3 in accordance with the present invention. Shown in a typical configuration (e.g., attached to a leg), the Ilizarov External Fixator 3 is comprised of a left full ring 4a and a right full ring 4b encircling a patient's limb (e.g., a femur), wherein said rings 4a and 4b are surgically implanted onto the limb by passing one or more wires 36 (see FIG. 4) through the bone and attaching said wires to connectors 33 located on each ring. Directing attention to FIGS. 1 and 4, the right full ring 4b contains a series of holes to accommodate threaded rods 5a and 5b. The left full ring 4a contains similar holes to accommodate the opposite ends of said threaded rods. In a preferred configuration, the threaded rods are positioned one above and one below the patient's limb so that clamping assemblies 2a and 2b can be attached to the right full ring 4b at points near 270° and 90°, respectively, around the circumference of said ring. The clamping assemblies 2a and 2b are attached to the right full ring at holes 9 using bolts 8 and nuts 10 (see FIGS. 4-6). Said clamping assemblies 2a and 2b are thereafter connected securely in position in order to adapt the adjustable splint device 1 to the Ilizarov External Fixator 3.

Referring to the figures, the adjustable splint device 1 is comprised of proximal struts 6 and 6a and distal struts 7 and 7a. The adjustable splint device 1 is adapted to the Ilizarov External Fixator 3 by passing said distal struts 7 and 7a through holes 14 (see FIGS. 4-6) in the centers of left clamping assembly 2a and right clamping assembly 2b, respectively, and tightening bolts 12 and nuts 16 which compress the clamping assemblies to hold distal struts 7 and 7a securely to the right full ring 4b. Although the configuration as shown provides clamping assemblies to connect the adjustable splint device to the Ilizarov External Fixator, it should be understood that any appropriate connecting means may be used to provide such an adaptation. For example, an Ilizarov ring could be manufactured providing a built in means for connecting the adjustable splint to the ring.

Referring to FIGS. 6-8, proximal strut 6 contains a rounded head portion 17 and distal strut 7 contains a socket head portion 19 which receives head portion 17 for pivotal engagement therewith. Rounded head portion 17 is cut away to define a cam surface 20 and is provided with an axial surface recess 23. A first surface plate 25 having a screw hole 27 covers one side of the combined head portions 17-19 and a second plate member 28 having a threaded protruding member 29 (see FIG. 8) covers the other half of the combined head portion 17-19. When surface plate member 28 is positioned over the combined head portion 17-19 protruding member 29 projects through the axial circular recess 23 and receives a screw 31 through screw hole 27. Proximal strut 6a and distal strut 7a are similarly pivotably connected by corresponding members bearing like numbers but carrying the distinguishing suffix "a".

The proximal and distal struts may be constructed of any material of sufficient strength such as plastic, metal, wood and the like. Particularly preferred are struts made of stainless steel metal. At least one of the struts should be at least partially hollow so as to house therein the adjustable spring mechanism of the invention. As shown in the drawings, the distal struts are tubular in construction and the proximal struts are solid. If desired, however, all of the struts can be tubular in construction so as to provide a lightweight product. Also if desired, each of the proximal struts 6 and 6a can be comprised of two telescoping portions as shown by the single proximal strut 6 depicted in FIG. 12 so as to permit lengthening and shortening of the proximal struts. Directing attention to FIG. 12, strut 6 is comprised of telescoping portions 150 and 151. The inner portion 150 is provided with a series of threaded holes 152 and the outer portion 151 with holes and threaded holes, respectively, through which screw 153 passes for threaded engagement with a coincident hole 152. Such a telescoping feature provides a splint which can be adjusted to several different lengths allowing the splint to fit a greater number of individuals. It should be understood that in this embodiment the splint device combination of the invention will include a series of spring abutting members 39 (see FIG. 8) of varying lengths so as to accommodate different limb lengths.

The adjustable spring-loaded mechanism designated generally as 30 may be provided in either the proximal or the distal struts. Preferably, however, it is the distal struts 7 and 7a that are provided with the adjustable spring mechanism.

The adjustable spring mechanism 30 is comprised of a spring 32 to which is attached a nose element 34 that bears on cam surface 20. Coil or clock springs are generally preferred but in some instances leaf springs are advantageously employed. An adjustable screw means indicated generally as 35 abuts the other end of the spring 32 and produces a quantifiable force which tends to either extend (i.e., align the proximal strut 6 with the distal strut 7 and proximal strut 6a with distal strut 7a in a parallel fashion) as shown in FIGS. 2 and 7 or to approximate (i.e., bring together the proximal strut 6 with the distal strut 7 and proximal strut 6a with distal strut 7a) as shown in FIG.

As maximum deflection or flexion is approached, tension is created in the compression coiled spring 32. The adjustable screw means 35 is comprised of an "Allen" head screw or slotted head screw 37 threaded to a spring-abutting member 39. The "Allen" head screw is fixed within distal strut 7 by screw 43. The "Allen" head screw 37 receives and is turned by an "Allen" socket wrench 42 (see FIG. 6) whereas a slotted head screw is adjustable with a conventional screwdriver blade. The turning of the screw creates greater compression of spring 32 thereby exerting greater force on the cam surface 20 of the proximal strut 6 to exert a one way tension. The tension capability of the spring mechanism can range from 0 pounds tension up to the maximum tension capability of the spring. In general, the tension of the spring mechanism will range from 0 pounds tension up to 10 pounds of tension and the tension exerted by the spring can be varied at any point of joint range of motion, say from 60° flexion to 0° flexion of the joint.

Whereas the specific joint range of motion to which tension can be exerted is preferred to be 60° flexion through 0° flexion for reducing flexion contractures in the knee and elbow, the joint range of motion at which tension can be applied can vary to nearly any degree in the 360° circular range simply by varying the point of attachment of the inner portion of strut 6 to rounded head portion 17 and by varying the point of attachment of strut 7 to socket head portion 19. Likewise, the same variations apply to struts 6a and 7a.

The purpose of varying the point in the joint range to which tension is applied is obvious when you consider that different illnesses and injuries cause different types of limitations at different degrees of joint ranges of motion thereby making necessary different points in the joint range at which tension must be applied to improve their condition. Another example would be when reducing an extension contracture of the knee the desired range of motion to which tension would be applied would range from 40° flexion to 130° flexion. The spring mechanism can be calibrated to exert the desired range of tension. The calibration can be effected by providing spring-abutting member 39 with a poundage indicator line 45 and a calibration scale 47 about the distal strut 7 which scale has a slot 49 through which the poundage indicator 45 is visible.

While the preferred adjustable biasing means of the invention is a spring means such as described, equivalent biasing means such as air or hydraulic powered biasing means will readily come to the mind of those skilled in this art.

Any suitable means can be utilized to secure pivotably mounted struts 6 and 6a to the limb so that they lie lateral to the joint with the axis of rotation coinciding as closely as possible to the axis of rotation of the joint. As shown in the figures, the securing means comprise a proximal cuff 51 attached to and extending between proximal strut 6 and proximal strut 6a. The length of the proximal cuff 51 is of sufficient distance to comfortably accommodate the limb part proximal to the limb joint. An overlying flap 55 is attached at one end to proximal strut 6a and contains on its outer surface an attaching means such as velcro hooks 56 by which the flap can wrap about the proximal portion of the limb and be secured to the velcro loops 57 on the outer surface of the proximal cuff wrapped about proximal strut 6. When wrapped around the limb and secured, the cuff serves as a counterforce strap.

It should be understood that a single combined strut, such as proximal strut 6 pivotably connected to distal strut 7, can alone be utilized as a splint device by securing proximal strut 6 by suitable means to the lateral side of the limb to be treated, and securing distal strut 7 by suitable means to the right full ring 4b of the Ilizarov External Fixator 3. Again, any suitable means for strapping or securing the splint device of the invention can be used, for example, by a proximal cuff of sufficient length to wrap around the proximal portion of the limb being treated. The strap 55 as well as the cuff 51 can be secured to the struts in any suitable manner as by sewing, tying, etc.

To facilitate the attachment of the cuff and strap, however, it is preferred that wire assemblies, designated generally in FIG. 9 as 72 and 76, be fastened as by welding to struts 6 and 6a, respectively. The wire assembly 72 is comprised of an upper thin wire portion 93 and a lower thin wire portion 92, each of which wire assembly portions extend from one end of strut 6a to the other. Similarly, wire assembly 76 is comprised of an upper thin wire portion 90 and a lower thin wire portion 91. In the preferred embodiment shown in FIG. 12 the shorter sides of the wire assemblies are of continuous construction and bent for more secure attachment as by welding to the struts. In the embodiment of FIG. 9 wire assembly 76 differs from wire assembly 72 in being of the "break apart" type as will be explained below so as to facilitate insertion and removal of the cuff or strap for cleaning, replacing, etc. Thus, wire assembly 76 is comprised of an upper thin wire portion 90 and a lower thin wire portion 91 both of which are broken at 97 and 98, respectively, so that the wire can be pulled apart slightly when the cuff or strap is to be attached or removed. In the embodiment of FIG. 12, however, both of the wire assemblies are of the "break apart" type, but one wire portion on the proximal struts, that is, two receiving wires contain telescoping sections B and B'. Telescoping sections B are internally threaded at one end for engagement with threaded ends B'. This gives the wire fixture added strength. Normally, a wire assembly with telescoping sections B and B40, however, is only used on the side of the strut which makes an angle of 65° when flexed.

When the adjustable splint is to be used for extension of a joint, a strap 120 is provided between struts 6 and 6a as shown in FIG. 9. Use of a strap 120 between struts 6 and 6a is often advisable in many instances; particularly in reducing knee flexion contractures. Strap 120 in these applications is important in order to maintain optimal alignment of the proximal struts along the parallel of the limb part proximal to the joint. Strap 120 also helps maintain the axis of rotation of the splint joint assembly more coincident with the axis of rotation of the body joint to which the splint is being applied.

Attachment of cuff 102, provided with a velcro hooks section 108 and a velcro loop section 110 as shown in FIG. 10, to the wire assemblies shown in FIG. 9 may then be conducted in the following manner:

Loop end section 104 of cuff 102 is put on wire portion 90 via break 97 with the velcro hooks section 108 and velcro loop section 110 facing outward. Edge 106 is taken over the limb and fed through and under wire portion 93 of wire assembly 72, and then put back on itself whereby velcro hooks 108 adhere to velcro loops 110. This secures one of the two cuffs needed to fix the splint assembly to a limb about a joint. The same procedure is used to attach a cuff or strap to the wire sections 91 and 92.

Where but a single assembly of a proximal and distal strut is to be used, the respective cuff and strap is provided near each of their ends with suitable securing means such as velcro hooks and loops. It should be understood that while the securing means are shown to be velcro closures, other alternative closures such as snaps and the like can be provided the cuff and strap.

Another novel cuff which can be used to secure the splint device to the limb is shown in FIGS. 13 and 14. Referring to these figures, the cuff 130 is of a length sufficient to accommodate a limb part proximal to the limb joint. The outside of cuff 130 is composed of a spaced apart and alternating velcro loop section 132 and a velcro hook section 134 each followed by a zone therebetween containing both velcro hook sections and velcro loop sections. Most advantageously, the zones containing both hook sections and loop sections are comprised of an intermediate area 138 constituted of a velcro loop or hook section identical to the preceding section, flanked on each side by areas having velcro loop or hook sections identical to the section of uniform velcro hooks or loops that follow. Thus, in FIG. 13, the zone following velcro loop section 132 is composed of an intermediate velcro loop area 138 flanked on each side by velcro hook areas 136. Velcro hook section 134, on the other hand, is followed by a zone having velcro hook area 142 flanked by velcro loop areas 143. If a longer cuff is required, the next zone would be of velcro loops only, etc.

Loop end section 144 of cuff 130 is provided with a stay-receiving means indicated generally as 146 into which is inserted a plastic stay 147 to prevent any collapsing that is likely to occur during use. Also, the inside of cuff 130 contains multiple stay receiving means 148. The cuff is shown in the figures as rectangular in shape. It should be understood, however, that the cuff can assume various curved configurations so as to conform to the particular limb to which it is attached. Attachment of cuff 130 to the wire assembly and the patient's limb can be effected as described above.

In a preferred embodiment of the invention, the splint device is provided with snap-on comfort pads shown in FIGS. 15 and 16. The comfort pads are of two types, the wedge-type of FIG. 15 and the rectangular-type of FIG. 16. The wedge-type comfort pad of FIG. 15 is composed of a wedge base 145 provided with a snap-on section comprised of a base plate 150 containing spaced snap-on elements 152 and 152'. The rectangular-type comfort pad of FIG. 16 is composed of a rectangular base 155 provided with a snap-on section comprised of a base plate 157 and snap-on elements 159 and 159'. The wedge base 145 and rectangular base 155 may be constructed of any suitable light weight material such as foamed plastic. The wedge-type comfort pads are used only when the adjustable splint of the invention is applied to the lower extremities, e.g., the leg below the knee. In this instance, two wedge-type comfort pads are normally snapped onto the proximal struts, within the wire assembly and between the limb and strut in a fashion whereby the thick portion of each wedge is proximal to the point of pivotable engagement of said struts.

The rectangular comfort pads are similarly snapped on the struts within the wire assembly and between the limb and the strut. Where the adjustable splint of the invention is applied to a lower extremity, two of the rectangular comfort pads will be placed on the lateral sides of the lower extremity, one on each of the proximal struts. On the other hand, where the adjustable splint is used on an upper extremity, e.g., an arm, the rectangular-type comfort pad will be used exclusively. In this case, normally two of the rectangular-type comfort pads will be snapped onto the proximal struts as set forth above, both on the lateral sides of the extremity.

The unique characteristics of the adjustable spring-loaded mechanism of the present invention is that it allows for adjustment of quantifiable force on an extremity acting across the body joint from 0 foot poundage up to the maximum foot poundage at various body joint ranges.

For example, in a patient having a knee flexion contracture of 30°, one may want to apply the splint to the knee and build in a tension of 5 foot pounds of force acting on the calf at 30° knee flexion angle. As the patient develops greater tolerance to the device, in days to come, greater force can be adjusted in the mechanism by simply adjusting the "Allen" wrench 42 and causing greater compression to the spring in the strut. This will exert a greater force toward extending the joint which will ultimately serve a more beneficial purpose in accomplishing reduction of the knee flexion contracture. On the other hand, if the patient has a flexion contracture of 45°, the same tension could be dialed into the splint at the angle just as could be done at 30° and just as could be done at a 10° knee flexion contracture. In other words, any force up to the maximum capability of the spring employed in the strut can be dialed at any angle of knee flexion. In addition, the invention permits the interchangeability of springs bearing force-exerting capabilities so as to allow for varying the degrees of tension exerted by the spring mechanism depending upon the particular use to which the device is applied. For a person with Quadriceps muscle weakness, a heavier gauged spring may be needed to allow for a greater force for extending the knee.

As an example of a particular case in which the adjustable splint for flexion of a joint might be used, one may consider an extension contracture, i.e., loss of ability to flex the joint through the normal range of motion, of any particular body joint such as the knee, elbow, etc. For simplicity the knee joint will be used.

In a knee extension contracture, whether the contracture is of a muscle or joint type, the individual may be able to flex the knee to 45° and no further. Applying the adjustable splint for flexion would be useful in that a force would be exerted on the body part proximal and distal to the knee which would tend to approximate the calf to the posterior thigh. The force exerted by the splint would be adjustable from 0 foot pounds of torque across the knee joint to upward torque of whatever tension capability the particular spring being used would have. A reasonable force would be to have an upper limit of 10–20 foot pounds acting at mid calf. The exact tension desired would be determined by factors such as patient tolerance, type and age of the contracture, skin compliance, diagnosis, etc.

Once the beginning tension and duration of splint application is determined, progression of the tension and duration can be accomplished by simple adjustment of the head screw 37 and increasing time, respectively.

With reference to FIG. 2, operation of the adjustable splint device in combination with the Ilizarov External Fixator of the invention, will now be described in connection with knee extension treatment following Ilizarov femoral surgery.

Within one week of the Ilizarov surgical procedure, the adjustable splint is connected to the Ilizarov External Fixator. First, the proximal cuff 51 is placed under the patient's calf and two wedge-type comfort pads as shown in FIG. 15 are positioned medially and laterally alongside the calf and within the proximal cuff (see FIG. 3). Slide the clamping assemblies 2a and 2b along distal struts 7 and 7a, respectively, until the clamping assemblies abut the Ilizarov right full ring 4b. After aligning the distal struts midline to the limb, connect the adjustable splint to the Ilizarov ring and tighten the clamping assemblies to hold securely the adjustable splint. In the appropriate configuration, the axis of the adjustable splint's joint should be concentric with the axis of the patient's knee joint, and the distal and proximal struts should lie midline to the patient's thigh and calf. Initially, the socket wrench 42 should be turned to set a reading of 1.0 on the calibration scale 47 (see FIG. 6). Following the third day after fitting of the adjustable splint, the tension read on the calibration scale may be advanced by ½ increment each day, unless the patient cannot tolerate additional tension or until the treatment is completed.

A unique feature of this adjustable splint device in combination with an Ilizarov External Fixator in the present application affixed to a leg or an arm, is the ability of this device to allow graduated, quantified, adjustable tension with the ability to relax the stretch across the joint by extending the knee or elbow away from the limit of flexion. This will allow the tissue being stretched to have a rest period while not disturbing the adjustment of the spring tension and without having to remove the splint. In order to relieve the pressure on the contractured tissues, one merely has to overcome, by any means, the tension in the splint and extend the joint to a comfortable posture. Once a short rest is achieved, the splint may again exert its tension against the contractured tissue to help accomplish a greater degree of flexion in the joint. In the case of a knee or elbow extension contracture, flexion would advance from the point of contracture, say 45° flexion, to the upper theoretical limits of flexion which, binding any other negating factors, would be 135–150. Time necessary to accomplish the optimal result using this splint would vary depending on many factors, some of which are the patient's diagnosis, extent of Ilizarov treatment involved, age of patient, age of the contracture and tolerance of the patient.

While the features of this invention have been disclosed with reference to the specific embodiments described herein, it is to be understood that various modifications may be made in the construction without departing from the scope of the invention as defined in the appended claims.

It is claimed:

1. An adjustable splint assembly comprised of an adjustable splint device and a fixator device, said adjustable splint device comprising a distal strut and a proximal strut pivotably connected to said distal strut, one of said struts having at one end a pivotably mounted head portion defining a cam surface, an adjustable biasing means mounted within the other strut and biased into engagement with said cam surface for applying a quantifiable force tending to align or approximate said distal and proximal struts, said fixator device comprising a right ring and a left ring, two or more surgical wires for implanting through a bone, with said wires connected at each end to the periphery of the right ring and crossing each other substantially near the center axis of said right ring, two or more surgical wires similarly connected to and crossing within the left ring, means for connecting said surgical wires to the right ring and left ring, an upper rod connected at one end to the left ring and at the other end to the right ring, a lower rod connected at one end to the left ring and at the other end to the right ring on the sides of the rings opposite the upper rod, means for connecting said upper rod and lower rod to the right ring and left ring, a clamping assembly slidably mounted on the distal strut of said adjustable splint device, means for securing said clamping assembly to the distal strut, means for connecting said clamping assembly to the right ring of said fixator device, and means for securing said adjustable splint assembly to a limb.

2. An adjustable splint assembly according to claim 1 wherein the adjustable biasing means is an adjustable spring means.

3. An adjustable splint assembly according to claim 2 wherein the adjustable spring means comprises a spring, a nose element connected to one end of said spring, an adjustable screw means engageable with the other end of said spring.

4. An adjustable splint assembly according to claim 3 wherein the adjustable screw means comprises a spring-abutting member, a screw member threadedly engaged in a threaded member fixed to said strut, one end of said screw member having a rotatable head and the other end of said screw member being engageable with said spring-abutting member.

5. An adjustable splint assembly according to claim 4 wherein the head is a socket.

6. An adjustable splint assembly according to claim 5 wherein the spring-abutting member is provided with an indicator marking.

7. An adjustable splint assembly according to claim 6 wherein the strut in which the adjustable spring means is mounted is hollow.

8. An adjustable splint assembly according to claim 7 wherein the hollow strut contains a slot having a scale along its length through which the screw member and indicator marking are visible, provided with a scale for setting the force to be applied.

9. An adjustable splint assembly according to claim 1 wherein at least one of the proximal struts is comprised of outer and inner telescoping portions, the outer telescoping portion being provided with a wire assembly for facilitating attachment of the splint assembly to the limb, said wire assembly comprising an upper wire portion and a lower wire portion, each of which extends substantially the length of and is attached to said outer telescoping portion, and means for fixedly securing together said telescoping portions.

10. An adjustable splint assembly according to claim 9 wherein the wire portions of the wire assembly taking the most pressure during use are provided with a reinforcing member which telescopes along the wire portion and is securable onto one split end of said wire portion.

11. An adjustable splint assembly according to claim 1 wherein the distal strut is of larger diameter than the proximal strut.

12. In combination, the adjustable splint assembly according to claim 9, wedge-shaped snap-on comfort pads provided on each of the proximal struts within the wire assembly on the medial side of the strut between the limb and strut and in a fashion whereby the thick portion of each wedge-shaped comfort pad is proximal to the point of pivotable engagement of said struts, and rectangular-type snap-on comfort pads provided on each of the proximal struts on the lateral side of the strut.

13. An adjustable spring-loaded splint assembly according to claim 9 wherein the means for securely holding the proximal parts of a limb between said pair of proximal struts comprises an elongate cuff member having on the outside thereof at least one velcro loop section spaced apart from at least one velcro hook section, said loop and hook sections each being followed by a zone therebetween containing both velcro hook and velcro loop sections.

14. An adjustable spring-loaded splint assembly according to claim 13 wherein the zone between the spaced apart velcro hook and loop sections is comprised of an intermediate area constituted of a velcro loop section or hook section identical to the preceding section, flanked on each side by areas having a velcro loop section or a velcro hook section identical to the section of velcro hooks or loops that follows.

15. An adjustable spring-loaded splint assembly according to claim 9 wherein the cuff end section is provided on the outside thereof with stay-receiving means for receipt of a stay that extends substantially the width of the cuff and wherein the inside of the cuff is provided with a plurality of spaced apart stay-receiving means positioned along the length of the cuff for receipt of stays that extend substantially the width of the cuff.

* * * * *